(12) United States Patent
Evans et al.

(10) Patent No.: US 6,333,183 B1
(45) Date of Patent: Dec. 25, 2001

(54) **DIDEOXYNUCLEOTIDE-TRIPHOSPHATE UTILIZATION BY THE HYPER-THERMOPHILIC DNA POLYMERASE FROM THE ARCHAEON *PYROCOCCUS FURIOSUS***

(75) Inventors: Steven Evans, Gosforth (GB); Joseph Anthony Mamone, Somerset; Maria Davis, Princeton, both of NJ (US); Bernard A. Connolly, Kingston Park (GB)

(73) Assignee: Amersham Pharmacia Biotech, Inc., Piscataway, NJ (US)

( * ) Notice: Subject to any disclaimer, the term of this patent is extended or adjusted under 35 U.S.C. 154(b) by 0 days.

(21) Appl. No.: 09/715,524

(22) Filed: Nov. 17, 2000

Related U.S. Application Data (60) Provisional application No. 60/167,066, filed on Nov. 23, 1999.

(51) Int. Cl.$^7$ .............................. C12N 9/12; C12N 9/00; C12P 19/34; C07K 1/00; C07H 21/04
(52) U.S. Cl. ................. 435/194; 435/183; 435/320.1; 435/252.3; 435/325; 435/91.1; 435/91.2; 530/350; 536/23.2
(58) Field of Search ................................ 435/194, 183, 435/320.1, 252.3, 325, 91.1, 91.2; 536/23.2; 530/350

(56) References Cited

U.S. PATENT DOCUMENTS

| | | |
|---|---|---|
| 5,489,523 | 2/1996 | Mathur . |
| 5,827,716 | 10/1998 | Mamone . |

FOREIGN PATENT DOCUMENTS

| | | |
|---|---|---|
| 0 655 506 A1 | 5/1995 | (EP) . |
| 0 727 496 A2 | 8/1996 | (EP) . |
| WO 99/06538 | 2/1999 | (WO) . |

OTHER PUBLICATIONS

Evans, S., et al. "Improving Dideoxynucleotide–Triphosphate Utilisation by the Hyper–Thermophilic DNA Polymerase from the Archaeon *Pyrococcus furiosus*" Nucleic Acids Research, vol. 28, No. 5, Mar. 1, 2000, pp. 1059–1066.

Gardner, A., et al. "Determinants of Nucleotide Sugar Recognition in an Archaeon DNA Polymerase" Nucleic Acids Research, vol. 27, No. 12, Jun. 15, 1999, pp. 2545–2553.

*Primary Examiner*—Kenneth R. Horlick
*Assistant Examiner*—Alexander H. Spiegler
(74) *Attorney, Agent, or Firm*—Royal N. Ronning, Jr.

(57) ABSTRACT

Polymerases from the Pol I family which are able to efficiently use ddNTPs have demonstrated a much improved performance when used to sequence DNA. A number of mutations have been made to the gene coding for the Pol II family DNA polymerase from the archaeon *Pyrococcus furiosus* with the aim of improving ddNTP utilisation. "Rational" alterations to amino acids likely to be near the dNTP binding site (based on sequence homologies and structural information) did not yield the desired level of selectivity for ddNTPs. However, alteration at four positions (Q472, A486, L490 and Y497) gave rise to variants which incorporated ddNTPs better than the wild type, allowing sequencing reactions to be carried out at lowered ddNTP:dNTP ratios. Wild type Pfu-Pol required a ddNTP:dNTP ratio of 30:1; values of 5:1 (Q472H), 1:3 (L490Y), 1:5 (A486Y) and 5:1 (Y497A) were found with the four mutants; A486Y representing a 150-fold improvement over the wild type. A486, L490 and Y407 are on an α-helix that lines the dNTP binding groove, but the side chains of the three amino acids point away from this groove; Q472 is in a loop that connects this α-helix to a second long helix. None of the four amino acids can contact the dNTP directly. Therefore, the increased selectivity for ddNTPs is likely to arise from two factors: 1) Small overall changes in conformation that subtly alter the nucleotide triphosphate binding site such that ddNTPs become favoured; 2) interference with a conformational change that may be critical both for the polymerisation step and discrimination between different nucleotide triphosphates.

9 Claims, 5 Drawing Sheets

(2 of 5 Drawing Sheet(s) Filed in Color)

Fig. 1A

Pol I  R(X)$_3$K(X)$_3$E(X)$_3$YG

Pol α  Q(X)$_3$K(X)$_3$N(X)$_2$YG

P α-helix

Tgo 470 TIDPIEKKLLDYRQRAIKILANSFYGYYGYAK
Pfu 471 TQDPIEKILLDYRQKAIKLLANSFYGYYGYAK

Pfu pol exo⁻ DNA sequence

| Sequence | Base pairs |
|---|---|
| ATGATTTTAGATGTGGATTACATAACTGAAGAAGGAAAACCTGTTATTAGGCTATTCAAAAAAGAGAACG<br>TACTAAAATCTACACCTAATGTATTGACTTCTTCCTTTTGGACAATAATCCGATAAGTTTTTTCTCTTGC | Base pairs<br>1-70 |
| GAAAATTTAAGATAGAGCATGATAGAACTTTTAGACCATACATTTACGCTCTTCTCAGGGATGATTCAAA<br>CTTTTAAATTCTATCTCGTACTATCTTGAAAATCTGGTATGTAAATGCGAGAAGAGTCCCTACTAAGTTT | Base pairs<br>71-140 |
| GATTGAAGAAGTTAAGAAAATAACGGGGGAAAGGCATGGAAAGATTGTGAGAATTGTTGATGTAGAGAAG<br>CTAACTTCTTCAATTCTTTTATTGCCCCCTTTCCGTACCTTTCTAACACTCTTAACAACTACATCTCTTC | Base pairs<br>141-210 |
| GTTGAGAAAAAGTTTCTCGGCAAGCCTATTACCGTGTGGAAACTTTATTTGGAACATCCCCAAGATGTTC<br>CAACTCTTTTTCAAAGAGCCGTTCGGATAATGGCACACCTTTGAAATAAACCTTGTAGGGGTTCTACAAG | Base pairs<br>211-280 |
| CCACTATTAGAGAAAAAGTTAGAGAACATCCAGCAGTTGTGGACATCTTCGAATACGATATTCCATTTGC<br>GGTGATAATCTCTTTTTCAATCTCTTGTAGGTCGTCAACACCTGTAGAAGCTTATGCTATAAGGTAAACG | Base pairs<br>281-350 |
| AAAGAGATACCTCATCGACAAAGGCCTAATACCAATGGAGGGGGAAGAAGAGCTAAAGATTCTTGCCTTC<br>TTTCTCTATGGAGTAGCTGTTTCCGGATTATGGTTACCTCCCCCTTCTTCTCGATTTCTAAGAACGGAAG | Base pairs<br>351-420 |
| GATATAGAAACCCTCTATCACGAAGGAGAAGAGTTTGGAAAAGGCCCAATTATAATGATTAGTTATGCAG<br>CTATATCTTTGGGAGATAGTGCTTCCTCTTCTCAAACCTTTTCCGGGTTAATATTACTAATCAATACGTC | Base pairs<br>421-490 |
| ATGAAAATGAAGCAAAGGTGATTACTTGGAAAAACATAGATCTTCCATACGTTGAGGTTGTATCAAGCGA<br>TACTTTTACTTCGTTTCCACTAATGAACCTTTTTGTATCTAGAAGGTATGCAACTCCAACATAGTTCGCT | Base pairs<br>491-560 |
| GAGAGAGATGATAAAGAGATTTCTCAGGATTATCAGGGAGAAGGATCCTGACATTATAGTTACTTATAAT<br>CTCTCTCTACTATTTCTCTAAAGAGTCCTAATAGTCCCTCTTCCTAGGACTGTAATATCAATGAATATTA | Base pairs<br>561-630 |
| GGAGACTCATTCGCATTCCCATATTTAGCGAAAAGGGCAGAAAAACTTGGGATTAAATTAACCATTGGAA<br>CCTCTGAGTAAGCGTAAGGGTATAAATCGCTTTTCCCGTCTTTTTGAACCCTAATTTAATTGGTAACCTT | Base pairs<br>631-700 |
| GAGATGGAAGCGAGCCCAAGATGCAGAGAATAGGCGATATGACGGCTGTAGAAGTCAAGGGAAGAATACA<br>CTCTACCTTCGCTCGGGTTCTACGTCTCTTATCCGCTATACTGCCGACATCTTCAGTTCCCTTCTTATGT | Base pairs<br>701-770 |
| TTTCGACTTGTATCATGTAATAACAAGGACAATAAATCTCCCAACATACACACTAGAGGCTGTATATGAA<br>AAAGCTGAACATAGTACATTATTGTTCCTGTTATTTAGAGGGTTGTATGTGTGATCTCCGACATATACTT | Base pairs<br>771-840 |
| GCAATTTTTGGAAAGCCAAAGGAGAAGGTATACGCCGACGAGATAGCAAAAGCCTGGGAAAGTGGAGAGA<br>CGTTAAAAACCTTTCGGTTTCCTCTTCCATATGCGGCTGCTCTATCGTTTTCGGACCCTTTCACCTCTCT | Base pairs<br>841-910 |
| ACCTTGAGAGAGTTGCCAAATACTCGATGGAAGATGCAAAGGCAACTTATGAACTCGGGAAAGAATTCCT<br>TGGAACTCTCTCAACGGTTTATGAGCTACCTTCTACGTTTCCGTTGAATACTTGAGCCCTTTCTTAAGGA | Base pairs<br>911-980 |
| TCCAATGGAAATTCAGCTTTCAAGATTAGTTGGACAACCTTTATGGGATGTTTCAAGGTCAAGCACAGGG<br>AGGTTACCTTTAAGTCGAAAGTTCTAATCAACCTGTTGGAAATACCCTACAAAGTTCCAGTTCGTGTCCC | Base pairs<br>981-1050 |
| AACCTTGTAGAGTGGTTCTTACTTAGGAAAGCCTACGAAAGAAACGAAGTAGCTCCAAACAAGCCAAGTG<br>TTGGAACATCTCACCAAGAATGAATCCTTTCGGATGCTTTCTTTGCTTCATCGAGGTTTGTTCGGTTCAC | Base pairs<br>1051-1120 |
| AAGAGGAGTATCAAAGAAGGCTCAGGGAGAGCTACACAGGTGGATTCGTTAAAGAGCCAGAAAAGGGGTT<br>TTCTCCTCATAGTTTCTTCCGAGTCCCTCTCGATGTGTCCACCTAAGCAATTTCTCGGTCTTTTCCCCAA | Base pairs<br>1121-1190 |
| GTGGGAAAACATAGTATACCTAGATTTTAGAGCCCTATATCCCTCGATTATAATTACCCACAATGTTTCT<br>CACCCTTTTGTATCATATGGATCTAAAATCTCGGGATATAGGGAGCTAATATTAATGGGTGTTACAAAGA | Base pairs<br>1191-1260 |
| CCCGATACTCTAAATCTTGAGGGATGCAAGAACTATGATATCGCTCCTCAAGTAGGCCACAAGTTCTGCA<br>GGGCTATGAGATTTAGAACTCCCTACGTTCTTGATACTATAGCGAGGAGTTCATCCGGTGTTCAAGACGT | Base pairs<br>1261-1330 |
| AGGACATCCCTGGTTTTATACCAAGTCTCTTGGGACATTTGTTAGAGGAAAGACAAAAGATTAAGACAAA<br>TCCTGTAGGGACCAAAATATGGTTCAGAGAACCCTGTAAACAATCTCCTTTCTGTTTTCTAATTCTGTTT | Base pairs<br>1331-1400 |
| AATGAAGGAAACTCAAGATCCTATAGAAAAAATACTCCTTGACTATAGACAAAAAGCGATAAAACTCTTA<br>TTACTTCCTTTGAGTTCTAGGATATCTTTTTTATGAGGAACTGATATCTGTTTTTCGCTATTTTGAGAAT | Base pairs<br>1401-1470 |
| GCAAATTCTTTCTACGGATATTATGGCTATGCAAAAGCAAGATGGTACTGTAAGGAGTGTGCTGAGAGCG<br>CGTTTAAGAAAGATGCCTATAATACCGATACGTTTTCGTTCTACCATGACATTCCTCACACGACTCTCGC | Base pairs<br>1471-1540 |

FIG. 4B

| Sequence | Base pairs |
|---|---|
| TTACTGCCTGGGGAAGAAAGTACATCGAGTTAGTATGGAAGGAGCTCGAAGAAAAGTTTGGATTTAAAGT<br>AATGACGGACCCCTTCTTTCATGTAGCTCAATCATACCTTCCTCGAGCTTCTTTTCAAACCTAAATTTCA | Base pairs<br>1541-1610 |
| CCTCTACATTGACACTGATGGTCTCTATGCAACTATCCCAGGAGGAGAAAGTGAGGAAATAAAGAAAAAG<br>GGAGATGTAACTGTGACTACCAGAGATACGTTGATAGGGTCCTCCTCTTTCACTCCTTTATTTCTTTTTC | Base pairs<br>1611-1680 |
| GCTCTAGAATTTGTAAAATACATAAATTCAAAGCTCCCTGGACTGCTAGAGCTTGAATATGAAGGGTTTT<br>CGAGATCTTAAACATTTTATGTATTTAAGTTTCGAGGGACCTGACGATCTCGAACTTATACTTCCCAAAA | Base pairs<br>1681-1750 |
| ATAAGAGGGGATTCTTCGTTACGAAGAAGAGGTATGCAGTAATAGATGAAGAAGGAAAAGTCATTACTCG<br>TATTCTCCCCTAAGAAGCAATGCTTCTTCTCCATACGTCATTATCTACTTCTTCCTTTTCAGTAATGAGC | Base pairs<br>1751-1820 |
| TGGTTTAGAGATAGTTAGGAGAGATTGGAGTGAAATTGCAAAAGAAACTCAAGCTAGAGTTTTGGAGACA<br>ACCAAATCTCTATCAATCCTCTCTAACCTCACTTTAACGTTTTCTTTGAGTTCGATCTCAAAACCTCTGT | Base pairs<br>1821-1890 |
| ATACTAAAACACGGAGATGTTGAAGAAGCTGTGAGAATAGTAAAAGAAGTAATACAAAAGCTTGCCAATT<br>TATGATTTTGTGCCTCTACAACTTCTTCGACACTCTTATCATTTTCTTCATTATGTTTTCGAACGGTTAA | Base pairs<br>1891-1960 |
| ATGAAATTCCACCAGAGAAGCTCGCAATATATGAGCAGATAACAAGACCATTACATGAGTATAAGGCGAT<br>TACTTTAAGGTGGTCTCTTCGAGCGTTATATACTCGTCTATTGTTCTGGTAATGTACTCATATTCCGCTA | Base pairs<br>1961-2030 |
| AGGTCCTCACGTAGCTGTTGCAAAGAAACTAGCTGCTAAAGGAGTTAAAATAAAGCCAGGAATGGTAATT<br>TCCAGGAGTGCATCGACAACGTTTCTTTGATCGACGATTTCCTCAATTTTATTTCGGTCCTTACCATTAA | Base pairs<br>2031-2100 |
| GGATACATAGTACTTAGAGGCGATGGTCCAATTAGCAATAGGGCAATTCTAGCTGAGGAATACGATCCCA<br>CCTATGTATCATGAATCTCCGCTACCAGGTTAATCGTTATCCCGTTAAGATCGACTCCTTATGCTAGGGT | Base pairs<br>2101-2170 |
| AAAAGCACAAGTATGACGCAGAATATTACATTGAGAACCAGGTTCTTCCAGCGGTACTTAGGATATTGGA<br>TTTTCGTGTTCATACTGCGTCTTATAATGTAACTCTTGGTCCAAGAAGGTCGCCATGAATCCTATAACCT | Base pairs<br>2171-2240 |
| GGGATTTGGATACAGAAAGGAAGACCTCAGATACCAAAAGACAAGACAAGTCGGCCTAACTTCCTGGCTT<br>CCCTAAACCTATGTCTTTCCTTCTGGAGTCTATGGTTTTCTGTTCTGTTCAGCCGGATTGAAGGACCGAA | Base pairs<br>2241-2310 |
| AACATTAAAAAATCCTAG<br>TTGTAATTTTTTAGGATC | Base pairs<br>2311-2328 |

DIDEOXYNUCLEOTIDE-TRIPHOSPHATE UTILIZATION BY THE HYPER-THERMOPHILIC DNA POLYMERASE FROM THE ARCHAEON *PYROCOCCUS FURIOSUS*

This application claims benefit of Provisional Application Ser. No. 60/167,066 filed Nov. 23, 1999.

FIELD OF INVENTION

The instant disclosure pertains to DNA polymerase mutants from Pyrococcus furiosus which exhibit improved dideoxynucleotide utilization.

BACKGROUND OF INVENTION

Figure 1A:
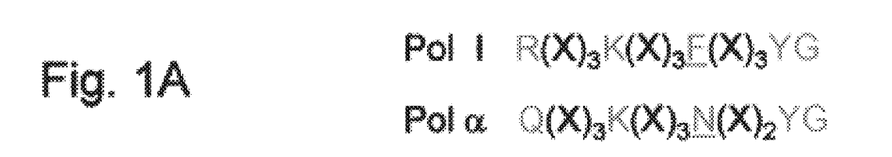
Figure 1B:
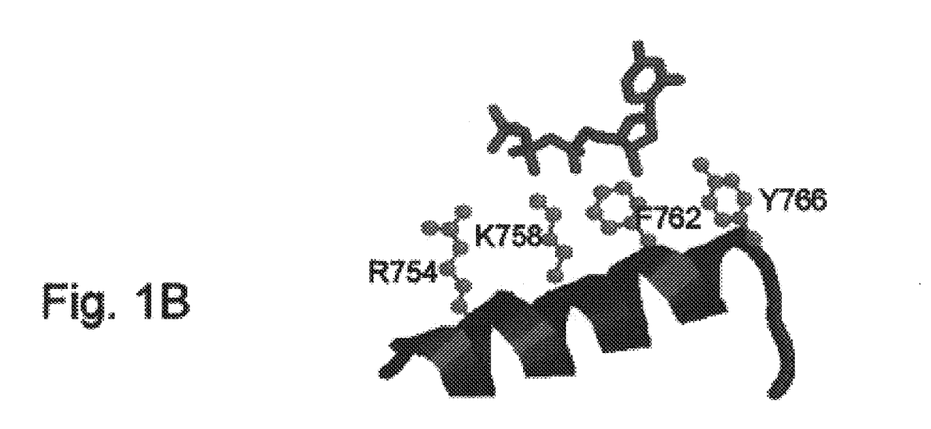
Figure 1C:
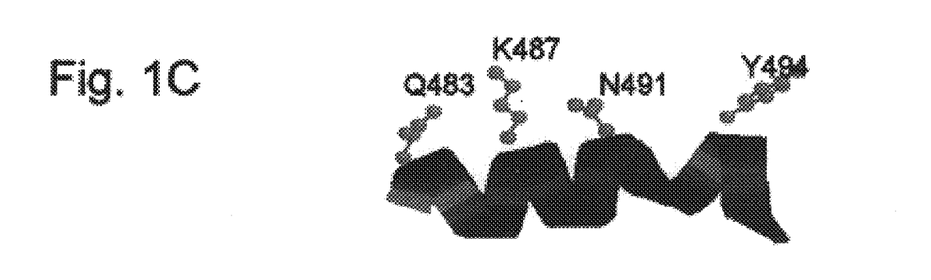

A polymerases constitute a core component of DNA sequencing methods, a widespread and important biotechnology, based on chain-termination by dideoxynucleotide-triphosphates (ddNTPs), either the ddNTPs themselves or fluorescent derivatives. Discrimination between chain-terminating ddNTPs and dNTPs plays a key role in DNA sequencing performance. Effective ddNTP incorporation is associated with a high uniformity of signal intensity in sequencing ladders. Furthermore, efficient usage of ddNTPs requires lower concentrations; an advantage when fluorescent terminators are used, as large excesses give rise to high backgrounds. Bacteriophage T7 DNA polymerase incorporates ddNTPs much more efficiently than the enzymes from *E. coli* and *T. aquaticus* and, as a consequence, gives superior sequencing ladders. The molecular basis for discrimination between dNTPs and ddNTPs resides in a single amino acid, at an equivalent location: Y526 (T7); F762 (*E. coli*); F667 (*T. aquaticus*). The T7 mutant, Y526F, shows a much reduced ability to use ddNTPs and, consequently, gives poor sequencing ladders. The F762Y and F667Y variants of *E. Coli* and *T. aquaticus* use ddNTPs effectively and show much improved sequencing properties. The important role of F762, in the *E. coli* polymerase, for deoxynucleotide-triphosphate recognition has been confirmed by a more complete kinetic analysis. Mutants of *T. aqualicus* DNA polymerase which have exonuclease activity removed, and contain tyrosine at position 667, have excellent sequencing properties and are perhaps the most widely used enzymes for DNA sequencing; these include Thermo-Sequenase™ and Amplitaq FS™ DNA polymerases. All three polymerases belong to the Pol-I family (also called family A polymerases) and the critical aromatic amino acid is found in a highly conserved stretch, the B-motif (also called region III)(FIG. 1). Structural data has shown that the B-motiff amino acids form an α-helix (the O-helix in the case of *E. coli*) with the most conserved amino acids on one side of the helix, forming part of the dNTP binding site (FIG. 1). The tyrosine/phenylalanine is near the sugar of the dNTP, rationalising its critical role in dNTP/ddNTP selection.

Polymerases with thermal stability are routinely used for DNA sequencing. Not only are they generally more robust than mesophilic enzymes but are essential for cycle-sequencing protocols, which involve heat-cool cycles. The extreme thermostability of polymerases purified from hyper-thermophilic archaea suggest these enzymes have potential use in DNA sequencing. However, archaeal polymerases often use ddNTPs poorly and, as a result, are generally not as useful in DNA sequencing as, for example, Thermo Sequenase™ DNA polymerase. Archaeal polymerases belong to the α-family (also called the B-family, or Pol-II family), a different group to the better characterised Pol-I enzymes. However, sequence alignment shows that the Pol-α family also has a B-motif, even though it cannot be exactly aligned with that of Pol-I (FIG. 1), and there is no exact counterpart to the aromatic amino acid critical for ddNTP/dNTP selection in the Pol-I family. Nevertheless, mutations in the B-motif of α-polymerases influence dNTP binding, suggesting a role in deoxynucleoside-triphosphate recognition. Recently, crystal structures of two Pol-α members, bacteriophage RB69 gp43 and *Thermococcus gorgonarius* (Tgo), have been published. The B-motif amino acids form an α-helix (the P-helix with both enzymes) which, as suggested by sequence alignments, is similar, but not structurally identical to the corresponding α-helix in the Pol-I family (FIG. 1). Although both structures lack bound nucleic acid it was possible to model primer-template and dNTP into RB69. The B-region was located near both primer/template and dNTP but did not appear to provide an amino acid that binds near the sugar of the dNTP. Rather, this might be supplied by tyrosine 416, an amino acid from another part of the polymerase, which packs under the sugar ring of the dNTP.

Sequence and structural comparisons of Pol-I and Pol-α members indicate that homologous regions are used for dNTP binding and recognition. However, the exact details of the interaction with dNTPs, and hence discrimination between dNTPs and ddNTPs, differs between the two classes. Therefore, the simple tyrosine/phenylalanine switch, so successful in converting *T. aquaticus* to a good sequencing polymerase, is unlikely to be possible with archaeal polymerases.

SUMMARY OF INVENTION

The instant invention comprises *Pyrococcus furiosus* polymerase mutants that recognise ddNTPS a factor of up to 150 fold better and are superior for cycle-sequencing protocols than the wild type enzyme. Methods for the isolation and characterisation of these mutants are discussed. The mutants exhibit superior thermal stability compared to other thermostable DNA polymerases, exhibiting stability for hours at 95° C. (compared with 30–45 minutes for *t. aquaticus* polymerase), thereby permitting a greater number of cycles at elevated temperature and, hence, enhanced sensitivity.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 1.A: The B-motif (region III) of polymerases from the Pol-I and Pol-α families. With Pol-I the R, K, F and YG indicated in green, and the spacing between them, are highly conserved. The F, shown in green and underlined, is critical in discrimination between dNTPs and ddNTPs. In the case of Polα the Q, K, N and YG shown in green, and their spacing, are conserved. It is difficult to deduce the optimal line up, between the two families, due to variation in both the conserved amino acids and their spacing. The alignment shown (others are possible by including gaps) has the critical F in Pol-I replaced by an N (underlined) in Pol-α.

FIG. 1.B: Structure of the B-motif of a Pol-I enzyme; the *E. Coli* Klenow fragment. The conserved amino acids (side chains shown in green) lie on one side of an α-helix and interact with dNTP (shown in red). F762 is near the sugar ring explaining its role in dNTP/ddNTP selection.

FIG. 1.C: Structure of the B-motif of the Pol-α enzyme from *Thermococcus gorgonarius*. Although the conserved amino acids (green) are on one side of an α-helix, as for Pol-I, the side chains, and their relative disposition, differ between the two families and are unlikely to interact with dNTPs identically. The α-helix of Tgo-Pol is also distorted by the presence of a short stretch of $3_{10}$-helix between N491 and Y494, resulting in a further difference between the two families. All structures were generated using RasMol.

FIG. 2.A: The amino acids in, and surrounding, the B-region of *Thermococcus gorgonarius* (Tgo) and *Pyrococcus furiosus* (Pfu) polymerases. The amino acids shown in green are highly conserved and correspond to the amino acids also illustrated in green in FIG. 1. Amino acids shown in magenta, when mutated in Pfu-Pol, give better sequencing performance. Note: Pfu-Pol contains a single amino acid insertion, upstream of this region, when compared to Tgo-Pol. This accounts for the numbering of corresponding amino acids differing by one.

FIG. 2.B: The structure formed by the Pfu-Pol amino acids shown in part A, which comprises an α-helix (the P-helix) flanked by loop regions (shown in blue). The conserved, green, amino acids (q484, K488, N492 and Y495) lie on one side of the helix and form part of the dNTP binding site. Three of the "improving", magenta, amino acids (A486, L490 and Y497) lie in the helical region but on the opposite side to the conserved amino acids. The fourth (Q472) is in a stretch of loop that precedes the α-helix. The side chains of these amino acids are shown in space-filling mode.

FIG. 2.C: End-on view of the P-helix region of Pfu-Pol clearly showing that the side chains (shown in space-filling mode) of the conserved (green) and "improving" (magenta) amino acids protrude on opposite sides of the helix. All structures were generated using RasMol.

FIG. 4 is the nucleotide sequence corresponding to Pfu pol exo⁻.

DETAILED DESCRIPTION OF INVENTION

The following illustrates certain preferred embodiment of the invention, but is not intended to be illustrative of all embodiments,
Methods and Materials
Construction of a Pfu-Pol Expression Vector A gene coding for Pfu-Pol (FIG. 4) was digested from the plasmid pTM121 (prepared in house by Amersham Pharmacia Biotech Inc.) as a NdeI-SmaI fragment and ligated into NdeI-EcoRV cut pET-17b (Novagen) to give pET-17b (Pfu-Pol). This manipulation destroys the unique EcoRV restriction site present in pET-17b.

The Pfu-Pol gene used contains the mutation D215A, which abolishes the 3' to 5' exonuclease activity of the enzyme. All experiments were performed with the exo⁻ form of the enzyme.
Expression and Purification of Pfu-Pol

*E. coli* BL21(DE3) (Novagen) containing pET-17b(Pfu-Pol) was grown at 37° C. until an $A_{600}$ of 0.5 was reached. Protein expression was induced by adding IPTG, to a final concentration of 1 mM, and continuing growth for another 4 hours. Cells were harvested by centrifugation at 4° C. (5,000 rpm for 20 minutes) and resuspended in 10 mM Tris pH8.0, 100 mM NaCl, 1 mM PMSF, 1 mM benzamidine. After sonication on ice (10×15s pulses) samples were centrifuged at 10,000 rpm for 20 minutes. The supernatant was incubated with approximately 20 units of DNase I (Boehringer-Mannheim) for 30 minutes to hydrolyse DNA. Next the supernatant was heated at 75° C. for 20 minutes to denature most of the *E. coli* proteins and inactivate the DNase I. Precipitated proteins were removed by centrifugation (10,000 rpm for 20 minutes) and the supernatant was loaded onto a 20 ml DEAE-Sephacel column, equilibrated and eluted with Tris pH 8.0, 100 mM NaCl. The flow through was collected and immediately applied to a 20 ml Heparin-Sepharose column, equilibrated with Tris pH 8.0, 100 mM NaCl. The column was developed with a 100 mM–700 mM NaCl gradient in Tris pH 8.0. Fractions were analysed by SDS-PAGE using Coomassie-Blue staining and those containing a protein running at approximately 90 kD were pooled and concentrated using Centriprep 50 spin concentrators (Amicon). Protein samples were estimated to be >95% pure as judged by SDS-PAGE. All purified protein samples were stored at −20° C. as 50% glycerol stocks.
Random Mutagenesis of Pfu-Pol and Selection of Mutants by Colony Screening Random mutagenesis was carried out on a section of the Pfu-Pol gene (in pET-17b) flanked by unique EcoRV and SacI restriction sites; a region comprising bases 1293–1596 and amino acid 431–532 (i.e. the P-helix and surrounding amino acids). A PCR-based method in conjunction with the mutagenic base analogues 8-oxo-dGTP and dPTP was used. The mutagenic primers used were GAACTAT-GATATCGCTCC (SEQ ID NO: 4)(EcoRV primer) and CTTTTCTTCGAGCTCCTTCCATACT (SEQ ID NO: 5)(SacI primer). Initially 30 rounds of PCR were carried out under the following conditions: 10 mM Tris-HCl, pH 8.8, 50 mM KCl, 1.5 mM $MgCl_2$, 0.08% Nonidet P-40, 500 μM each dNTP (four normal and two mutagenic), 0.5 units of *T. aquaticus* DNA polymerase; cycle 94° C.—1 min., 55° C.—3 min., 72° C.—2 min. The amplified products were used in a second PCR reaction (conditions identical to the first but with only the four normal dNTPs at 250 μM) to generate a library of mutated DNA fragments. The library was digested with EcoRV and SacI and ligated into pET-17b(Pfu-Pol) from which the EcoRV-,SacI fragment of the wild-type Pfu-Pol gene had been excised. The resulting plasmids were used to transform *E. Coli* BL21(DE3) to ampicillin resistance. Transformants containing Pfu-Pol variants better able to incorporate ddNTPs were selected by modifying a "colony screening rapid filter assay" usually used to detect DNA polymerase activity. Bacterial colonies were gridded onto duplicate LB/ampicillin agar plates and allowed to grow overnight at 37° C. The colonies from one plate were replica-plated onto a nitrocellulose filter containing activated calf-thymus DNA, which was then overlaid onto an LB/ampicillin plate containing 1 mM IPTG. After a further 4 hours, at 37° C., during which Pfu-Pol expression was induced, the nitrocellulose filters were removed and cells lysed using toluene/chloroform. The nitrocellulose filters were soaked in 20 mM Tris-HCl, pH 8.5, 10 mM KCl, 20 mM $(NH_4)_2SO_4$, 2 mM $MgSO_4$, 0.1 mg/ml bovine serum albumin and 0.1% Nonidet P-40 and baked at 70° C. for 30 min. to destroy *E. coli* DNA polymerases. The filters were re-soaked with this buffer but also containing 12 μM each of dTTP, dCTP and dGTP plus 1 μl of [α-$^{32}$P]-ddATP (3000 Ci/mmol, Nycomed-Amersham) and then incubated at 70° C. for 30 min. to allow $^{32}$P incorporation into polymeric material. The filters were washed with trichloroacetic acid and pyrophosphate, dried and any radioactivity retained on the filters (i.e. incorporated into polymeric material) determined using autoradiography (30). Under these conditions wild type Pfu-Pol results in minimal retention of $^{32}P$ on the filters. Clones that were associated with $^{32}P$ retention were rescued from the duplicate LB/ampicillin plate and used for both the preparation of mutant Pfu-Pol (exactly as for the wild type enzyme) and plasmid preparation for DNA sequencing.

Site-directed mutagenesis of Pfu-Pol

Site-directed mutagenesis of the Pfu-Pol gene was carried out using the PCR-based "overlap extension" method (31). Most of the directed mutants were made to the P-helix i.e. within the EcoRV/SacI fragment described above. Therefore the EcoRV and SacI oligonucleotides were used as the common outer primers, along with appropriate primers containing the required mutation, produce two overlapping DNA fragments. These two fragments, containing the desired mutation, were used as a template in a subsequent PCR reaction, together with the EcoRV and SacI primers to generate the "full-length" mutated EcoRV/SacI fragment. The protocol for PCR and the subsequent cloning of the mutated fragment were as described above. The amino acid Y410 is not in the P-helix and so does not lie between the EcoRV and SacI restriction sites. The mutations Y410F/A were produced analogously using an EcoRI flanking primer (GGGAAAGAATTCCTTCC) (SEQ ID NO: 6) and the SacI primer. The Y410 codon is located between the unique EcoRI and SacI restriction sites.

DNA Sequencing Using Pfu-Pol Mutants

DNA sequencing reactions were performed using cycle-sequencing. A kit purchased from Stratagene (Exo-"Cyclist" DNA sequencing kit) together with M13 mp18 single stranded template DNA and a universal primer was used. Approximately 1–2 units of mutant polymerase was added per sequencing reaction, corresponding to the amount of wild type Pfu-Pol normally used. Reactions were initially performed at a 30:1 ddNTP/dNTP ratio, the optimal nucleotide ratio for the wild type enzyme. This ratio was progressively lowered for mutant enzymes that showed an increased preference for dideoxynucleotides.

Results

Figure 2A:
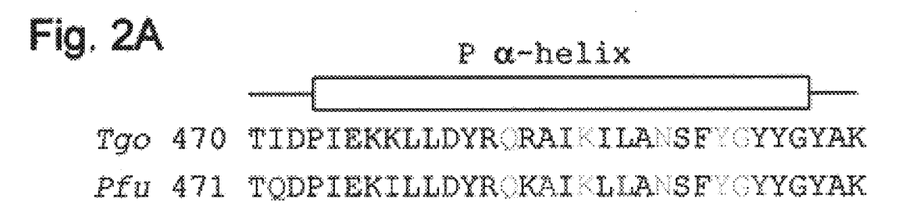
Figure 2B:
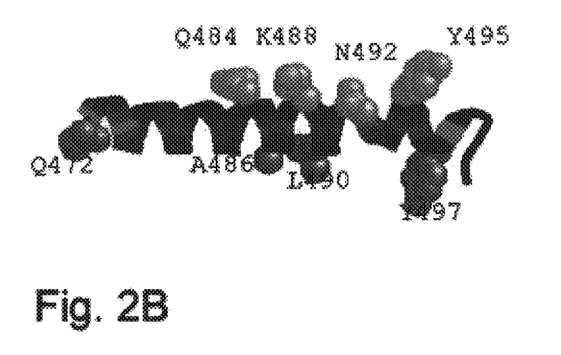
Figure 2C:
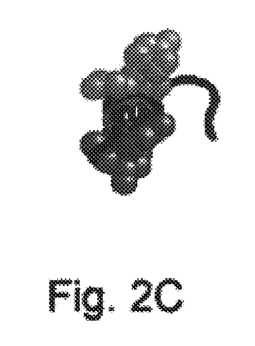

Although the B-region in polymerases belonging to the Pol-I and Pol-α families are similar, rather than identical, it is clear that both play a role in dNTP binding. The amino acid sequence in the vicinity of the B-region for *Pyrococcus furiosus* polymerase (Pfu-Pol), the enzyme investigated in this study, is shown in FIG. 2. For comparison the homologous sequence of the structurally characterised *Therimococcus gorgonarius* enzyme (Tgo-Pol) is also shown. With Tgo-Pol The B-motif consists of an α-helix (The P-helix) flanked by loop regions (FIG. 2). Tgo-Pol and Pfu-Pol have 79% sequence identity and variant amino acids invariably involve highly conservative changes. We have used Swiss-Model/SwissPdb viewer to deduce a structure for Pfu-Pol based on Tgo-Pol. As expected the two structures are almost identical and the derived P-helix from Pfu-Pol is shown in FIG. 2. A variety of mutations has been made to these amino acids in Pfu-Pol (Table 1), using either random mutagenesis or back-to-back PCR site-directed mutagenesis (31). The mutants were expressed in *E. Coli*, using pET-17b, and purified using a heat step, followed by two chromatography columns. All proteins appeared pure by heavily-loaded SDS-PAGE, stained with Coomassic-Blue.

Figure 3:
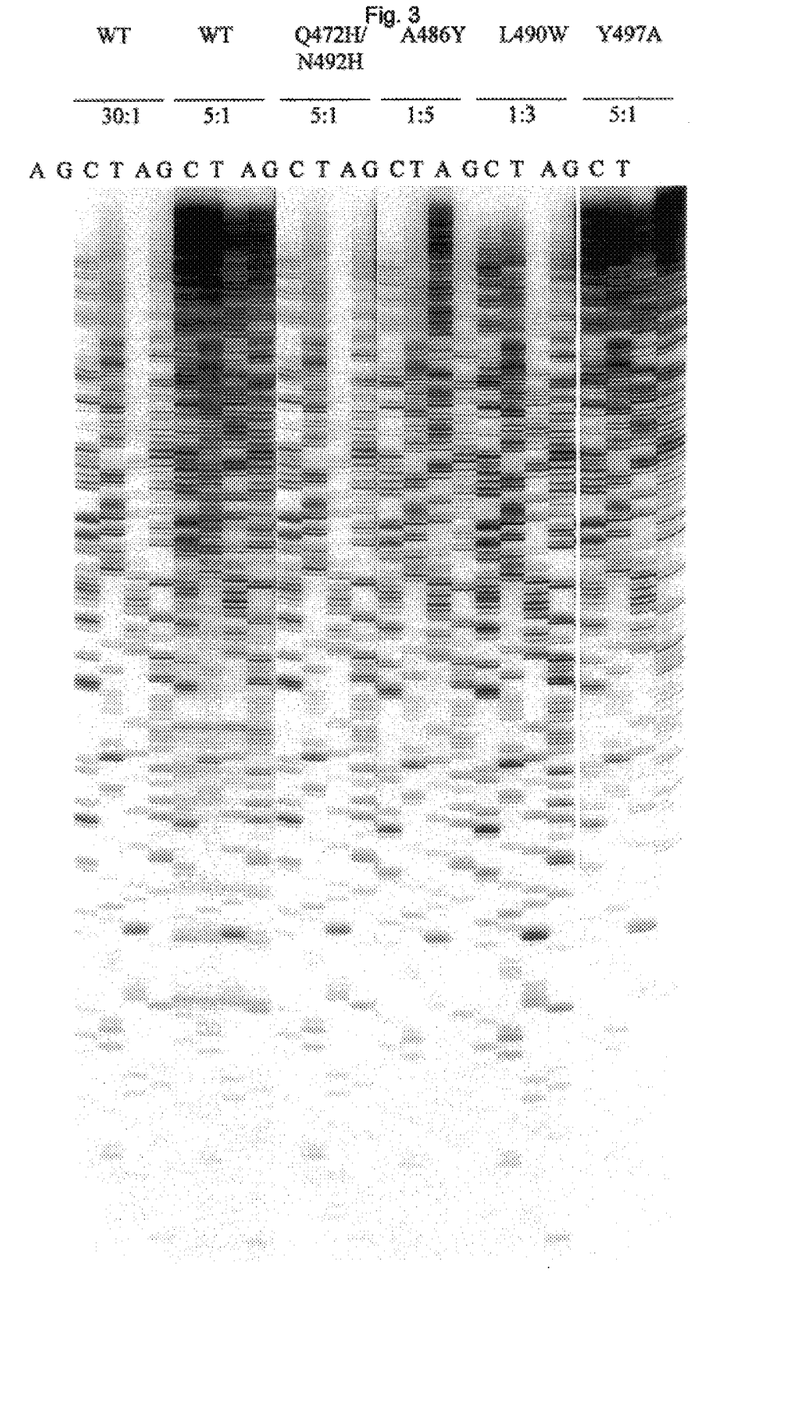
FIG. 3 is a sequencing gel in which the dideoxynucleotide-triphosphate utilization of wild type DNA polymerase from *Pyrococcus furiosus* is compared against DNA polymerase from *Pyrococcus furiosus* mutants Q472H/N492H, A486Y, L490W, and Y497A.

The DNA-sequencing performance of the mutants was assessed using a standard cycle-sequencing protocol with the four $[\alpha-^{32}P]$-ddNTPs as chain terminators. In our hands wild-type Pfu-Pol gave good sequencing ladders (clearly defined bands, lack of non-specific termination, sequencing information spread over the entire size range of fragments) at a ddNTP:dNTP ratio of 30:1 (FIG. 3). However, when a 5:1 ratio was used much of the radioactivity was found towards the top of the gel (due to lower than optimal levels of termination giving rise to long products) and excessive non-specific termination was also seen, resulting in shadow bands across all four lanes. Both effects make it impossible to deduce the DNA sequences from the sequencing ladders. As improved DNA-sequencing performance correlates with increased selectivity for ddNTPs, we looked for mutants that give a readable sequencing ladder at ddNTP:dNTP ratios of <30:1. Therefore, mutants were initially tested at the wild-type 30:1 ratio. Enzymes which gave readable sequencing gels or were associated with increased radioactivity towards the bottom of the gel (indicative of better ddNTP incorporation resulting in shorter products) were then evaluated at a 5:1 ratio of ddNTP:dNTP and, if warranted, at progressively decreasing ratios of the two triphosphates.

Initially, the four most highly conserved amino acids (Q484, K488, N492, Y495), on the side of the P-helix that faces the ddNTP binding site (FIGS. 1 and 2), were investigated. Most of the mutants showed inferior sequencing ladders at the 30:1 ddNTP:dNTP ratio used for initial screening, when compared to the wild type enzyme (Table 1). The few mutants that appeared equivalent to the wild type under these conditions all gave unreadable sequencing gels, characterised by radioactivity towards the top of the gel and non-specific termination, at a 5:1 ratio of trinucleotides. Both sequence and structural comparisons (FIG. 1) show that the Pol-α family does not have an exact counterpart to the critical phe/tyr found with Pol-I enzymes. The best guess as to which amino acid, if any, would play this role is N492; a residue that is highly conserved and structurally at least in a similar location to the phe/tyr (FIG. 1). However, N492Y (i.e. an attempt to introduce a tyr near a location shown to give good sequencing performance with the Pol-I family) gave an inactive enzyme. Other mutations to this amino acid, e.g. N492H/K/G, while active resulted in difficult to read ladders at the initial 30:1 ddNTP:dNTP ratio. Changes to Q484, K488 and Y495 gave sequencing phenotypes at best equivalent to, but more commonly worse than, the wild type enzyme (Table 1).

As shown in FIG. 1, not only do the conserved amino acids on the same side of the O- or P-helix vary in the nature of their side chains but also in the spacing between them. The B-motif in the Pol-α family is missing an amino acid when compared to Pol-I. Alternative alignments to that shown in FIG. 1, in which a gap in Pol-α is placed opposite the key phe/tyr in Pol-I, have been proposed. Therefore, insertion mutations consisting of: addition of single tyrosine immediately before N492 (A(Y)N); replacement of several Pfu-Pol P-helix amino acids with the corresponding regions of the *T. aquaticus* O-helix (TIN(Y)GVL) (Table 1), have been prepared. In these Pfu-Pol variants the "missing" amino acid is replaced with a tyrosine either in the Pfu-Pol or the *T. aquaticus* polymerase context, allowing a more exact sequence alignment of the mutated B-motif with that of the Pol-I family. These insertion mutations also represent another approach to placing a tyrosine near the important phe/tyr in the pol-I family. Unfortunately, all insertion mutations were inactive (Table 1).

Following alterations to the conserved amino acids and variation in their spacing a number of mutations have also been made in most of the other P-helix amino acids. As can be seen in Table 1 the majority of the changes lead to a sequence performance roughly equivalent to the wild type polymerase i.e. readable ladders at ddNTP:dNTP ratios of 30:1, no useful sequencing data, with most radioactivity at the top of the gel and non-specific termination at the 5:1 ratio. Therefore, most changes offered no improvement in DNA sequencing performance over that of the wild type. Three mutations A486Y, L490W and Y497A, were found which gave readable sequencing ladders at the 5:1 ratio. Progressively decreasing the amount of chain terminator showed that A486Y could be used at a ddNTP:dNTP ratio of 1:5, L490W at 1:3 and Y497A at 5:1; representing an improvement over wild type (in terms of ddNTP usage) of 150, 90 and 6 fold respectively (Table1, FIG. 3). Other mutations to these amino acids e.g. L490Y and Y497W also resulted in preferential usage of ddNTPs when compared to the wild type, although the ddNTP:dNTP ratios useable with these mutants were not as good as with L490W and Y497A respectively. We also found certain mutations to these amino acids e.g. A486W and Y497F (Table 1) that resulted in poorer ddNTP utilisation as compared to the wild type enzyme.

As well as changing the amino acids in the P-helix in a directed manner, random mutagenesis has been used between amino acids 431 and 532. This stretch of 101 amino acids encompasses the P-helix as well as amino acids flanking this structural element (FIG. 2). Preparing large number of random mutants is quick and straightforward; screening for improved phenotype is often more tedious and difficult. We have adapted a "colony screening rapid filter assay", originally used to identify recombinants containing wild type *T. aquaticus* DNA polymerase, to directly assess improved incorporation of ddNTPs. Essentially *E. coli* colonies, on nitrocellulose filters containing activated calf-thymus DNA, are incubated with [$\alpha$-$^{32}$P]-ddATP and dTTP/dCTP/dGTP. Colonies expressing a Pfu-Pol mutant that effectively uses ddNTPs transfer radioactivity to polymeric DNA immobilised on the nitrocellulose filter, allowing subsequent detection by autoradiography. The method includes a heat step, prior to the assay, to destroy host polymerases and so automatically scores for thermostability in the mutant Pfu-Pol. Only one mutant, that appeared to incorporate ddNTPs particularly well, was found and revealed by sequencing to be a double mutant, Q472H-N492H. This double mutant gave good sequencing data at a ddNTP:dNTP ratio of 5:1 (Table 1) i.e. a 5-fold improvement over wild type. However, the amount of ddNTP could not be further decreased and so the double mutant does not appear to be as good as either A486Y or L490W. The amino acid at 492, normally asparagine, is one of the conserved P-helix amino acids, described above (FIGS. 1 and 2). We therefore thought that the improvement in phenotype was due to the N492H change, a combination not tested above. Remarkably single directed mutants showed that the key change was to Q472H, which gave good sequencing ladders, equivalent to those produced by the double mutant at 5:1 ddNTP:dNTP ratios. The single mutant N492H showed non-specific termination at the 5:1 ratio and in fact gave slightly inferior performance to the wild type when tested at 30:1 ddNTP-:dNTP. The amino acid Q472 is located in a loop that connects the P-helix to another long $\alpha$-helix (FIG. 2) and its location is such that it is unlikely to interact directly with dNTPs. Not only does the mutation Q472H improve ddNTP incorporation but it fully rescues a mutant, N492H, with sequencing performance worse than the wild type.

Changes have also been made to Y410, an amino acid that is not in the P-helix, but has been shown by crystallography to have an important role in binding dNTPs, forming the bottom of the nucleotide binding cleft. In our hands both Y410F and Y410A offered no improvement over the wild type (Table 1).

Attempts to further reduce the amount of ddNTP needed for sequencing, by combining the improved mutants A486Y, L490W and Q472H-N492H were unsuccessful. One double mutant A486Y-L490W behaved in an identical manner to the single mutant A486Y i.e. gave readable sequencing gels at 1:5 ddNTP:dNTP (Table 1). The other two, A486Y-Q472H-N492H and L490W-Q472H-N492H, actually gave worse sequencing performance, characterised by unreadable gels at ddNTP:dNTP ratios of 1:5 and 1:3, than was seen with A486 and L490W alone.

Thus, it has been seen that with the Pol-I enzymes a change of a single phe to a tyr converts ddNTPs from very poor to very good substrates. It was suggested that the 3'—OH of the natural dNTP substrate was one of the ligands for the essential Mg$^{2+}$, required for polymerisation. With ddNTPs, which lack a 3'—OH, this interaction cannot take place, accounting for their poor substrate properties. Most Pol-I enzymes contain a phe, near the sugar of the dNTP, which is sometimes (either in a few natural Pol-I enzymes e.g. from T7 or by site-directed mutagenesis) replaced by tyr.

Further, changes to most of the amino acids likely to interact directly with the dNTP do not improve discrimination for ddNTPs over dNTPs. This includes the conserved amino acids on one side of the P-helix and Y410 (FIGS. 1 and 2, Table 1). None of the mutations improve ddNTP incorporation and sequencing performance (or else give low specific activities rendering the question of improved properties irrelevant) and an effect as profound as that caused by the single phe/try switch with the Pol-I family was never observed. Additionally, inserting a single amino acid into the P-helix of Pfu-Pol (to produce a better alignment with the O-helix of Pol-I) or helix swaps between the two categories gave inactive enzyme. This probably arises because of a large overall disruption to Pol-$\alpha$ structure when its P-helix is replaced with the equivalent of an O-helix. Finally, changes to most of the other, less conserved, amino acids in the P-helix also lead to no improvement in selectivity for ddNTP and DNA sequencing performance (Table 1).

Changes at three positions within the P-helix, amino acids A486, L490 and Y497 gives rise to a higher selectivity for ddNTPs. As shown in FIG. 2, the side chains of these amino acids protrude from the P-helix on the side facing away from the DNA-binding cleft. The three amino acids cannot, therefore, interact directly with the dNTP, as postulated for the four highly conserved amino acids, Q484, K488, N492 nad Y495. Mutagenesis of Vent™ polymerase also concluded that changes to the equivalent of the Pfu-Pol A486 (A488 in Vent™) lead to an increase in the efficiency of ddNTP usage. This study changed A488 to several alternatives and it was observed that the bigger the side chain, the better the utilisation of ddNTP. The largest side chain used in this study was phe and this lead to a boost in the incorporation of ddNTPs, by a factor of about 15-fold, evaluated using sequencing gels. The change we made, A486Y, allows readable sequencing gels at a ddNTP:dNTP ratio of 1:5, a 150-fold improvement over the wild type. The determination of "sequencing performance" by visual inspection of gels is somewhat subjective; even under optimised conditions with the wild-type enzyme, non-specific termination is visible in a few places. Therefore, deciding the ddNTP:dNTP ratio which gives clearly interpretable patterns i.e. exactly when non-specific termination begins to interfere with readability is difficult. However, we routinely use the Pfu-Pol A486Y mutant for sequencing purposes at the 1:5 ddNTP:dNTP ratio and find it gives reliable sequencing information. What is clear, though, is that this amino acid represents a residue important for ddNTP usage, even though any improvement is far less than the phe/tyr switch in the pol-I family. L490 is one turn along the helix form A486 and the side chains of these two amino acids point in almost identical directions (FIG. 2). This amino acid was not studied with Vent™ but we have found that the mutation L490W improves ddNTP usage, by a factor only slightly less than the A486Y change. L490Y, while slightly improved over wild type, is far less effective than L490W. This may, like the changes to the alanine described above, result from a correlation between side chain size and ddNTP utilisation. However, as there are not many larger side chains than the wild type leu, it is difficult to test this experimentally with a series of mutations as carried out with Vent™ polymerase and A488. Two other P-helix amino acids, L479 and Y497, have side chains that point in almost the same direction as those of A486 and L490. Changes to L479 give a phenotype similar to wild type (Table 1). However, some changes to Y497 (Y497W and Y497A) lead to a slightly improved preference for ddNTPs (Table 1), whereas others Y497F decrease ddNTP utilisation. A similar effect was seen with Vent™ with the corresponding amino acid Y499.

Not only are A488 and L490, the amino acids in the P-helix which when changed lead to the most pronounced preference for ddNTPs, unable to interact with dNTPs directly, but they are not highly conserved in the Pol-α family. Although the equivalent position to A486 is most usually ala, other amino acids e.g. asn, ser, ile, leu and phe are found. Similarly L490 is commonly replaced by either another hydrophobic amino acid or thr/ser. This non-conservation emphasises that A486 and L490 are unlikely to have a direct critical function e.g. binding dNTP, primer/template or in catalysis.

The indirect action of the mutants A488Y and L490W was confirmed by the detection of a third mutant, associated with better ddNTP usage. Random mutagenesis to a region including both the P-helix and its flanking sequences revealed the double mutant Q472H-N492H. The improved properties do not result from the change to N492 (the conserved N in the P-helix, FIGS. 1 and 2) but, as shown by subsequent single mutants (Table 1), to alteration to Q472. The residue Q472 is in a loop that lies between the P-helix and a second long α-helix. These two anti-parallel helices comprise the bulk of the fingers domain of the RB69 and Tgo (28) polymerases and presumably also of the Pfu-Pol. Q472 is highly variable between Pol-α enzymes and even differs within the more closely related archaeal sub-set of this class e.g. this residue is ile with Tgo-Pol and Vent™ (FIG. 2). Q472H, or the double mutant Q4721H-N492H, only improve ddNTP incorporation, as assessed by sequencing gels, by a factor of 6-fold.

It is apparent that many modifications and variations of the invention as hereinabove set forth may be made without departing from the spirit and scope thereof. The specific embodiments described are given by way of example only, and the invention is limited only by the terms of the appended claims.

TABLE 1

DNA sequencing properties of Pfu-Pol mutants.

| Category of enzyme | Mutant | ddNTP:dNTP ratio optimized for DNA sequencing ladders |
|---|---|---|
| Wild-type | Wild-type | 30:1 |
| Alterations to highly conserved amino acids In P-helix (shown in green in FIGS. 1 and 2) | Q484A | Worse than wild type |
| | K488A | Worse than wild-type |
| | N492H/K/G | Worse than wild-type |
| | N492Y | Inactive Enzyme |
| | Y495/I/D/C/S | Similar to wild-type |
| Insertions into P-helix* | A(Y)N and TIN(Y)GVL | Inactive enzyme |
| Alterations to other amino acids in P-helix (see FIG. 2) | L479Y/W/P | Similar to wild-type |
| | A486Y | 1:5 |
| | A486W | Worse than wild-type |
| | L490W | 1:3 |
| | L490Y | 5:1 |
| | S493Y | Similar to wild-type |
| | F494Y/C/S/T/V | Similar to wild-type |
| | G496P/S/A | Similar to wild-type |
| | Y497F | Worse than wild-type |
| | Y497W | 10:1 |
| | Y497A | 5:1 |
| Alterations to Y410 | Y410A/F | Worse than wild-type |
| Alterations to loop preceding the P-helix (see FIG. 2) | N492H | 5:1 |
| Multiple mutations | Q472H-N492H | 5:1 |
| | A486Y-L490W | 1:5 |
| | Q472H-A486Y-N492H | Worse than A486Y |
| | Q472H-L490W-N492H | Worse than L490W |

The wild-type enzyme gives readable DNA sequencing gels at a 30:1 ddNTP:dNTP ratio, but unreadable gels at 5:1. Mutants described as similar to wild-type have this property; mutants noted as worse give unreadable gels at the 30:1 ratio. For mutants with improved discrimination the number given is the lowest ratio of ddNTP:dNTP at which readable sequencing gels were obtained. Y410F/A indicates Y 410 was changed to both F and A etc. *A(Y)N has a Y inserted between A491 and N492. In TIN(Y)GVL this sequence replaces the amino acids between 489 and 494 (LLANSF).

What is claimed is:

1. A purified recombinant thermostable DNA polymerase comprising the amino acid sequence which corresponds to the nucleotide sequence of SEQ ID NO:1 further modified to contain one or more amino acid changes selected from the group consisting of Q472H/N492H, A486Y, L490W, L490Y, Y497A, Y497W, N492H, Q472H/N492H, and A486Y/L490Y.

2. An isolated nucleic acid that encodes a thermostable DNA polymerase having the amino acid sequence of claim 1.

3. A DNA polymerase encoded for by the nucleic acid of claim 2.

4. A recombinant DNA vector that comprises the nucleic acid of claim 2.

5. The recombinant vector of claim 4 containing the plasmid pTM121.

6. A recombinant host cell transformed with the vector of claim 4.

7. The recombinant host cell of claim 6, wherein the cell is *E. coli*.

8. In a method of sequencing DNA which comprises the step of generating chain terminated fragments from a DNA template to be sequenced with a DNA polymerase, the improvement comprising utilizing as said DNA polymerase the DNA polymerase of claim 1 in the presence of at least one chain terminating agent and one or more nucleotide triphosphates, and determining the sequence of said DNA from the sizes of said fragments.

9. A kit for sequencing DNA comprising the DNA polymerase of claim 1.

* * * * *

SEQUENCE LISTING

<160> NUMBER OF SEQ ID NOS: 6

<210> SEQ ID NO 1
<211> LENGTH: 2328

<212> TYPE: DNA
<213> ORGANISM: Pyrococcus furiosus

<400> SEQUENCE: 1

| | | | | | |
|---|---|---|---|---|---|
| atgattttag | atgtggatta | cataactgaa | gaaggaaaac | ctgttattag | gctattcaaa | 60 |
| aaagagaacg | gaaaatttaa | gatagagcat | gatagaactt | ttagaccata | catttacgct | 120 |
| cttctcaggg | atgattcaaa | gattgaagaa | gttaagaaaa | taacggggga | aaggcatgga | 180 |
| aagattgtga | gaattgttga | tgtagagaag | gttgagaaaa | agtttctcgg | caagcctatt | 240 |
| accgtgtgga | aactttattt | ggaacatccc | caagatgttc | ccactattag | agaaaaagtt | 300 |
| agagaacatc | cagcagttgt | ggacatcttc | gaatacgata | ttccatttgc | aaagagatac | 360 |
| ctcatcgaca | aaggcctaat | accaatggag | ggggaagaag | agctaaagat | tcttgccttc | 420 |
| gatatagaaa | ccctctatca | cgaaggagaa | gagtttggaa | aaggcccaat | tataatgatt | 480 |
| agttatgcag | atgaaaatga | agcaaaggtg | attacttgga | aaaacataga | tcttccatac | 540 |
| gttgaggttg | tatcaagcga | gagagagatg | ataaagagat | tctcaggat | tatcagggag | 600 |
| aaggatcctg | acattatagt | tacttataat | ggagactcat | cgcattccc | atatttagcg | 660 |
| aaagggcag | aaaaacttgg | gattaaatta | accattggaa | gagatggaag | cgagcccaag | 720 |
| atgcagagaa | taggcgatat | gacggctgta | gaagtcaagg | gaagaataca | tttcgacttg | 780 |
| tatcatgtaa | taacaaggac | aataaatctc | ccaacataca | cactagaggc | tgtatatgaa | 840 |
| gcaattttg | gaaagccaaa | ggagaaggta | tacgccgacg | agatagcaaa | agcctgggaa | 900 |
| agtggagaga | accttgagag | agttgccaaa | tactcgatgg | aagatgcaaa | ggcaacttat | 960 |
| gaactcggga | agaattcct | tccaatggaa | attcagcttt | caagattagt | tggacaacct | 1020 |
| ttatgggatg | tttcaaggtc | aagcacaggg | aaccttgtag | agtggttctt | acttaggaaa | 1080 |
| gcctacgaaa | gaaacgaagt | agctccaaac | aagccaagtg | aagaggagta | tcaaagaagg | 1140 |
| ctcagggaga | gctacacagg | tggattcgtt | aaagagccag | aaaagggggtt | gtgggaaaac | 1200 |
| atagtatacc | tagattttag | agccctatat | ccctcgatta | taattaccca | caatgttct | 1260 |
| cccgatactc | taaatcttga | gggatgcaag | aactatgata | tcgctcctca | agtaggccac | 1320 |
| aagttctgca | aggacatccc | tggtttata | ccaagtctct | gggacattt | gttagaggaa | 1380 |
| agacaaaaga | ttaagacaaa | aatgaaggaa | actcaagatc | ctatagaaaa | aatactcctt | 1440 |
| gactatagac | aaaaagcgat | aaaactctta | gcaaattctt | tctacggata | ttatggctat | 1500 |
| gcaaaagcaa | gatggtactg | taaggagtgt | gctgagagcg | ttactgcctg | gggaagaaag | 1560 |
| tacatcgagt | tagtatggaa | ggagctcgaa | gaaaagtttg | gatttaaagt | cctctacatt | 1620 |
| gacactgatg | gtctctatgc | aactatccca | ggaggagaaa | gtgaggaaat | aaagaaaaag | 1680 |
| gctctagaat | ttgtaaaata | cataaattca | aagctccctg | gactgctaga | gcttgaatat | 1740 |
| gaagggtttt | ataagagggg | attcttcgtt | acgaagaaga | ggtatgcagt | aatagatgaa | 1800 |
| gaaggaaaag | tcattactcg | tggtttagag | atagttagga | gagattggag | tgaaattgca | 1860 |
| aaagaaactc | aagctagagt | tttggagaca | atactaaaac | acggagatgt | tgaagaagct | 1920 |
| gtgagaatag | taaagaagt | aatacaaaag | cttgccaatt | atgaaattcc | accagagaag | 1980 |
| ctcgcaatat | atgagcagat | aacaagacca | ttacatgagt | ataaggcgat | aggtcctcac | 2040 |
| gtagctgttg | caaagaaact | agctgctaaa | ggagttaaaa | taaagccagg | aatggtaatt | 2100 |
| ggatacatag | tacttagagg | cgatggtcca | attagcaata | gggcaattct | agctgaggaa | 2160 |
| tacgatccca | aaaagcacaa | gtatgacgca | gaatattaca | tggagaacca | ggttcttcca | 2220 |

```
gcggtactta ggatattgga gggatttgga tacagaaagg aagacctcag ataccaaaag      2280
acaagacaag tcggcctaac ttcctggctt aacattaaaa aatcctag                   2328
```

<210> SEQ ID NO 2
<211> LENGTH: 32
<212> TYPE: PRT
<213> ORGANISM: Thermococcus gorgonarius

<400> SEQUENCE: 2

Thr Ile Asp Pro Ile Glu Lys Lys Leu Leu Asp Tyr Arg Gln Arg Ala
 1               5                  10                  15

Ile Lys Ile Leu Ala Asn Ser Phe Tyr Gly Tyr Tyr Gly Tyr Ala Lys
            20                  25                  30

<210> SEQ ID NO 3
<211> LENGTH: 32
<212> TYPE: PRT
<213> ORGANISM: Pyrococcus furiosus

<400> SEQUENCE: 3

Thr Gln Asp Pro Ile Glu Lys Ile Leu Leu Asp Tyr Arg Gln Lys Ala
 1               5                  10                  15

Ile Lys Leu Leu Ala Asn Ser Phe Tyr Gly Tyr Tyr Gly Tyr Ala Lys
            20                  25                  30

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 4

```
gaactatgat atcgctcc                                                    18
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 5

```
cttttcttcg agctccttcc atact                                            25
```

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 6

```
gggaaagaat tccttcc                                                     17
```